United States Patent [19]

Blackwell, III et al.

[11] 4,163,848

[45] Aug. 7, 1979

[54] PROCESS FOR THE PRODUCTION OF 2-ALKYL- OR CYCLOALKYL-4-METHYL-6-HYDROXYPYRIMIDINES

[75] Inventors: Joseph T. Blackwell, III, Greensboro; John T. Gupton, Jamestown; Teruko U. Miyazaki, Greensboro, all of N.C.; James B. Nabors, Baton Rouge, La.; Joseph R. Pociask, Greensboro, N.C.

[73] Assignee: Ciba-Geigy Corporation, Ardsley, N.Y.

[21] Appl. No.: 932,087

[22] Filed: Aug. 8, 1978

[51] Int. Cl.² .......................................... C07D 239/36
[52] U.S. Cl. ...................................... 544/319; 544/97
[58] Field of Search ........................................ 544/319

[56] References Cited

U.S. PATENT DOCUMENTS

| | | | |
|---|---|---|---|
| 3,997,536 | 12/1976 | Boller et al. | 544/319 |
| 4,012,506 | 3/1977 | Balke et al. | 544/319 |
| 4,014,879 | 3/1977 | Balke et al. | 544/319 |
| 4,018,771 | 4/1977 | Gupton et al. | 544/319 |
| 4,052,396 | 10/1977 | Pociask | 544/319 |
| 4,052,397 | 10/1977 | Blackwell et al. | 544/319 |

*Primary Examiner*—Donald G. Daus
*Assistant Examiner*—James H. Turnipseed
*Attorney, Agent, or Firm*—Karl F. Jorda

[57] ABSTRACT

Production of 2-alkyl- or cycloalkyl-4-methyl-6-hydroxypyrimidines by first neutralizing an alkyl imidate ester hydrochloride with a base in the presence of a water-immiscible solvent for the alkyl imidate ester to be freed thereby; condensing the alkyl imidate ester with diketene to form an oxazinone intermediate, which is then reacted in organic solution with gaseous ammonia and recovering the desired substituted 6-hydroxypyrimidine.

18 Claims, No Drawings

PROCESS FOR THE PRODUCTION OF 2-ALKYL- OR CYCLOALKYL-4-METHYL-6-HYDROXYPYRIMIDINES

FIELD OF THE INVENTION

The present invention relates to a new and improved manufacturing process for 2-alkyl- or 2-cycloalkyl-4-methyl-6-hydroxypyrimidines of the formula:

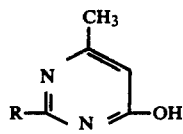
I wherein R represents an alkyl or cycloalkyl group.

Alkyl groups denoted by R are straight or branched chain lower alkyl groups having preferably 1 to 4 carbon atoms such as, methyl, ethyl, n-propyl, isopropyl, n-butyl, secondary butyl, isobutyl, or tertiary butyl.

Cycloalkyl groups denoted by R have 3 to 6 ring carbon atoms. Preferred cycloalkyl groups are cyclopropyl, cyclopentyl or cyclohexyl.

BACKGROUND OF THE INVENTION

The compounds of formula I are important intermediates for the preparation of, e.g., phosphoric acid esters of substituted hydroxypyrimidines as disclosed and claimed in U.S. Pat. No 2,754,243 and in particular 0,0-diethyl-0-(2-isopropyl-4-methyl-6-pyrimidyl)-thiophosphate (DIAZINON) which has great commercial value. It is a well-established insecticide and acaricide and is useful in pest control.

These substituted hydroxypyrimidines have been produced in commercial practice in a laborious multi-step manner as follows:

a) Iminoether Step:

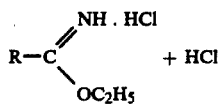

b) Amidine Step:

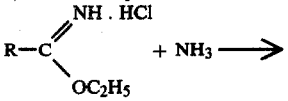
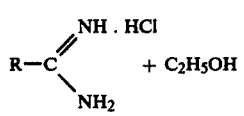

c) Ring-closure Step:

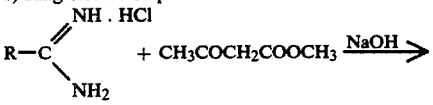
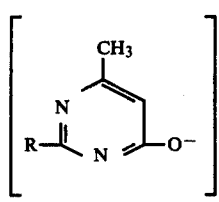

d) Neutralization Step:

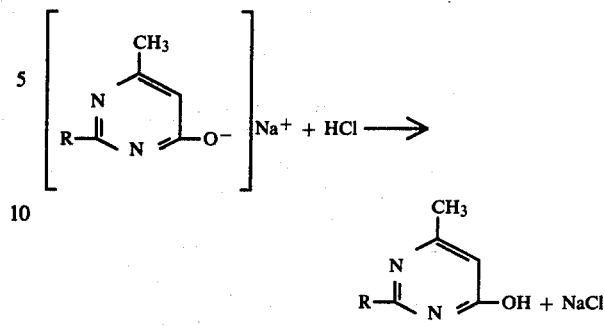

Recently the above conventional manufacturing process has been improved and optimized by a continuous ring-closure/neutralization process as claimed in U.S. Pat. No. 4,014,879, issued Mar. 29, 1977.

Alternate processes for the preparation of these hydroxypyrimidines have been published in the Japanese Patent literature. Japanese Pat. No. 557,103 teaches that these hydroxypyrimidines can be prepared by various heat treatments from β-acylaminocrotonamides prepared from β-aminocrotonamides (derived from diketene and ammonia) and acid halides or anhydrides. According to published Japanese Patent Application SHo-48-39-942 these hydroxypyrimidines can be prepared by reacting β-aminocrotonamide and an organic acid ester in the presence of certain alkaline reactants such as alkali metals or their alcoholates.

Recently there have been patented alternate ways of preparing the compounds of Formula I including U.S. Pat. No. 3,618,771, which issued Apr. 19, 1977 and U.S. Pat. No. 4,052,396 and U.S. Pat. No. 4,052,397, which issued on Oct. 4, 1977.

U.S. Pat. No. 4,018,771 teaches the synthesis of these compounds by reacting diketene with lower alkanoic acid amides in the presence of catalysts and then treating the resulting N-acetoacetyl alkanoic acid amides with ammonia in the presence of acidic catalysts.

U.S. Pat. No. 4,052,396 discloses the reaction of diketene with alkanoic acid nitriles in the presence of acidic catalysts followed by the treatment of the reaction product with ammonia.

U.S. Pat. No. 4,052,397 discusses the preparation of the hydroxypyrimidines of Formula I by sequentially treating, in organic solvent, diketene with ammonia and then treating the resulting β-aminocrotonamide, after water removal, with an alkanoic acid ester and an alkali metal alkoxide.

However, all of these prior art procedures leave something to be desired from the standpoint of efficient economical large-scale commercial manufacturing. It is an object of this invention to provide a better synthetic route to these materials.

THE INVENTION

The present invention provides a better and cheaper technology which unexpectedly is based upon the easily prepared imidate (imidine) hydrochloride intermediate of the earliest synthetic route and proceeds to prepare therefrom these products by simple steps, in batch or continuous processing, to yield the desired product in excellent yield and high purity. The process which proceeds easily under mild conditions comprises the steps of neutralizing an imidate hydrochloride of the formula:

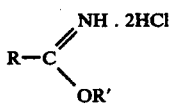

with an aqueous solution of a strong acid-accepting base in the presence of a water-immiscible solvent to obtain the free imidate. R is, as noted above, alkyl of 1 to 4 carbon atoms or cycloalkyl of 3 to 6 ring carbon atoms and R' is alkyl of 1 to 4 carbon atoms.

The organic phase containing the free imidate is separated from the aqueous phase and dried and the imidate is reacted with diketene in organic solution and in the presence of a catalyst to form an oxazinone having the formula:

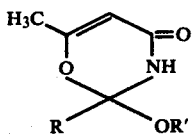

wherein R and R' are as above.

Upon completion of the diketene addition, the resulting oxazinone in organic solution is reacted with gaseous ammonia. Any water formed is removed and the 2-alkyl-4-methyl-6-hydroxypyrimidine recovered upon removal of the organic solvent in substantially pure form and excellent yield.

DETAILED DESCRIPTION OF THE INVENTION

The basic reaction scheme may be illustrated as follows:

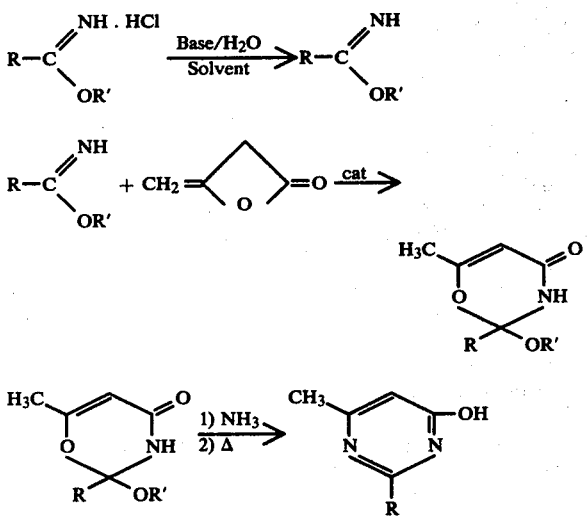

The starting imidate hydrochloride is available from the art as described in U.S. Pat. No. 2,754,243 and U.S. Pat. No. 4,014,879 and thus provide, via the method, starting materials for the various 2-alkyl- or cycloalkyl-4-methyl-6-hydroxypyrimidines of this invention.

Among such starting materials various imidate esters of formula II may be used, of which the methyl, ethyl, propyl and butyl groups can function as R' with the ethyl group being preferred.

The neutralization of the imidate ester salt procedes via reaction with a strong base. The base may be inorganic, such as, an alkali metal hydroxide and carbonate or an organic acid-acceptor base. Among the latter, trialkylamines of $C_{1-4}$ alkyl, such as, trimethylamine or triethylamine perform very well, with trimethylamine being preferred. Pyridine is also an excellent acid-acceptor base.

Among the water-immiscible solvents used to dissolve the neutralized (free) imidate are the liquid aromatic and aliphatic hydrocarbons and the liquid chlorinated hydrocarbons, including benzene, toluene, xylene, hexane, heptane, 1,1,1-trichloroethane, 1,1,2-trichloroethane, tetrachloroethylene, dichloromethane, ethylene dichloride with toluene being preferred as it subsequently provides greater ease in water removal.

A possible temperature range for this reaction step is $-30$ to $50°$ C.; a preferable range is $-10$ to $25°$ C. and a most preferable range is 0 to 10. However, if this reaction step is carried out continuously, the temperature should preferably range between 10 to $20°$ C.

The reaction time for this step may range between 5 to 120 minutes and preferably between 10 to 60 minutes.

The water removal ensures a purer product in better yield and thus is important in commercial practice. The water is initially removed by phase-separation of the immiscible organic solvent with the free imidate dissolved therein. Any residual water in the solvent is removed by azeotropic distillation or contact with drying agents, such as, molecular sieves or anhydrous drying salts, such as, anhydrous sodium sulfate. Of these drying steps, the contact driers are preferred in the laboratory but azeotropic distillation is preferred on an industrial scale.

The dry imidate base is then reacted with diketene to form the oxazinone. The imidate and the diketene preferably should be dissolved in solvents.

It is preferred if a mutual solvent, such as, toluene, tetrachloroethylene or trichloroethylene is used, but individual solvents for each component may be used if they are mutually miscible. Toluene is preferred.

The reaction between the free imidate and diketene is facilitated by the presence of Lewis acid- or Lewis base-catalysts, with pyridine and trialkylamines being preferred. In general, the catalysts can be used in amounts of 0.1 to 25 mole %; preferably they are used in amounts of 1 to 10 mole % and most preferably, 2.5 to 5 mole % of the reactants.

The amount of diketene used can also be in excess, preferably about or up to 5 mole %; greater excesses are of no advantage.

The reaction forming the oxazinone is exothermic and thus the reaction vessel should be cooled as it has been noted that the oxazinone begins to decompose at about $40°$ C. Cooling the vessel to below $35°$ C. ensures good yields of high purity, particularly for the economically most valuable 2-isopropyl-4-methyl-6-hydroxypyrimidine. Thus, the temperature for this reaction can range between $0°$ to $60°$ and preferably between $15°$ to $35°$ C. and the reaction is completed within three hours.

The oxazinone is then reacted with gaseous ammonia to form the hydroxypyrimidine of formula I. Kato et al, *Yakugaku Zassi* 92, 886 (1972) have reported at page 889 the preparation of 2-isopropyl-6-methyl-4(3H)-pyrimidone by reacting the respective oxazinone with aqueous ammonia water in ethyl alcohol. However, the reaction scheme with organic solvents for gaseous dry ammonia provides better yields of a higher purity product, which when converted to the final product meets color standards and overall purity of product requirements of the government agencies in charge of certification of this final product.

The reaction of the oxazinone with the gaseous ammonia in toluene is carried out at a temperature ranging between 0° and 60° C. and preferably 15° to 35° C. and is completed within three hours. Any water resulting from the conversion of the oxazinone is removed by azeotropic distillation and the pyrimidine is recovered in 98+% yield. The reaction from the oxazinone to the pyrimidine with the gaseous ammonia is postulated to proceed as follows:

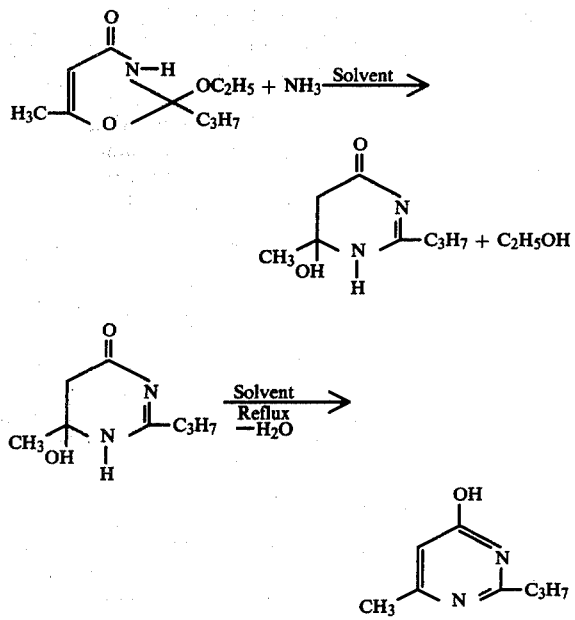

It is the removal of the water from the intermediate between the oxazinone and the pyrimidine which provides the superior product of the present invention.

The invention will be more specifically illustrated in the appended examples which are directed to the preparation according to this invention of the economically most important compound 2-isopropyl-4-methyl-6-hydroxypyrimidine known in the trade as "oxypyrimidine". The examples represent the preferred mode and alternative modes and are applicable to the preparation not only of the isopropyl "oxypyrimidine" but to the other alkyl- and cycloalkyl-pyrimidines of this invention.

It should be understood that various changes and modifications in the procedures described above generally and exemplified below specifically can be made, such changes and modifications being within the scope of the appended claims. It should further be understood that the following examples illustrating specific embodiments are not intended to limit the claims.

Temperatures are given in degrees centigrade.

EXAMPLE 1

A 2-l three-necked, round-bottom flask was equipped with a mechanical stirrer, thermometer and addition funnel. Into the flask was placed 452 g (4.60 moles) of a 60% aqueous solution of trimethylamine. The solution was cooled to 5° with an ice bath and a solution of 199 g of ethyl isobutyrimidate hydrochloride (1.00 moles of imidate and 2.30 moles of hydrogen chloride) in 500 ml of toluene was added to the flask at such a rate that the reaction temperature remained below 10°. After the addition was completed, the phases were separated and the organic phase was placed in a 1-l, three-necked, round-bottom flask which had been equipped with a mechanical stirrer, thermometer, 1 ft. packed column, water trap and condenser. The mixture was heated slowly at atmospheric pressure and the trimethylamine was allowed to vent without condensation. The toluene-water azeotrope was condensed and the distillation was continued until the boiling point of the distillate reached 110°. The yield of imidate (material in pot) was 98.6% and the resulting solution contained 0.8 mole percent water.

EXAMPLE 2

A 500 ml, 5-necked flask was equipped with a mechanical stirrer, thermometer, addition funnel and a condenser with a water trap. A solution of 56.4 g (0.96 mole) of trimethylamine in 46 g of $H_2O$ was charged and to this was added dropwise a mixture of 44.9 g of ethyl isobutyrimidate hydrochloride (containing 0.2 mole of ethyl isobutyrimidate) and 80 ml of tetrachloroethylene solvent over a four minute period. The temperature was maintained at $-12°$ to $4°$ during the addition. After the addition was complete, the phases of the reaction mixture were separated, and the $H_2O$ in the organic phase was removed by azeotropic distillation at atmospheric pressure. The dry solution (228 g) contained by weight 10.25% ethyl isobutyrimidate and resulted in a yield of 99.8%.

EXAMPLE 3

In a 2-l, 3-necked flask which was equipped with a mechanical stirrer, thermometer, addition funnel and dry ice-acetone bath was placed 182.44 g (1.32 moles) of potassium carbonate in 500 ml of water. Ethyl isobutyrimidate hydrochloride (112.6 g containing 0.5 mole of ethyl imidate and 1.32 moles of hydrogen chloride) was diluted with 200 ml of toluene and was added dropwise over a 7 minute period while maintaining the temperature below $-8°$. The solution was stirred at $-9°$ for an additional 30 minutes during which 300 ml of water was added to dissolve the potassium chloride precipitate. After the phases were separated the aqueous phase was extracted with 50 ml of toluene and the combined toluene phases were dried by azeotropic distillation using a 1 ft. packed column. The solution in the distillation flask weighed 234.82 g and contained 23.6% of ethyl isobutyrimidate and 1.1 mole % water. The yield of ethyl isobutyrimidate was 97.8%.

EXAMPLE 4

A 1-l, 3-necked flask was equipped with a mechanical stirrer, thermometer, addition funnel and dry ice-acetone bath. Methyl isobutyrimidate hydrochloride (106.8 g) which contained 0.523 moles of methyl imidate and 1.282 moles of hydrogen chloride was mixed with 20 ml of toluene and cooled. A 25% aqueous solution of trimethylamine (606 g, 2.56 moles) was added over a period of 10 minutes while maintaining the reaction temperature below 5°.

After the solution was stirred for 5 minutes without the cooling bath, the layers were separated. The aqueous layer was extracted with 2×50 ml of toluene and the toluene phases were combined. Trimethylamine and water contained in the toluene phase were distilled out azeotropically under 95 mm of Hg using a 1 ft. packed column and a Dean-Stark distilling trap. After the water in the Dean-Stark trap was removed and the toluene phase was returned to the flask, 2 g of sodium sulfate was placed in the bottom of the trap and distillation was resumed. The distillate in the trap was returned to the flask. The solution weighed 265.06 g and contained 20.6% of methyl isobutyrimidate and 2.1 mole % of water. The yield of methyl isobutyrimidate was 99.7%.

EXAMPLE 5

Into a 3-l, three-necked, round-bottom flask, equipped with a mechanical stirrer, thermometer, addition funnel and ice bath was placed 971.61 g (4.11 M.) of 25%, aqueous trimethylamine. The solution was cooled to 5° and 347.39 g (1.00 M.) of a 33.2% solution of ethyl isobutyrimidate hydrochloride in toluene was added dropwise over 1 hr. and 20 min. while maintaining the reaction temperature at 5°-6°. After the addition was completed the solution was stirred for an additional 15 min., and the phases were separated. The aqueous phase was extracted with 150 ml. of toluene, the combined organic phases were dried over anhydrous sodium sulfate and filtered. The sodium sulfate was washed with 50 ml of toluene.

The combined filtrates weighed 413.57 g and contained 25.8% ethyl isobutyrimidate (92.5% yield). The solution was placed under reduced pressure to remove the excess trimethylamine, and the resulting solution (27.2% imidate) was dried over anhydrous magnesium sulfate.

EXAMPLE 6

A 3-l, three necked, round-bottom flask was equipped with a mechanical stirrer, thermometer and addition funnel. Into the flask was placed 1189 g (5.04 M) of a 25% solution of trimethylamine. The solution was cooled to 5° to 10°, and a mixture of 207.65 g (1.00 M) of a 48.7% solution of methyl isobutyrimidate hydrochloride and 500 ml of methylene chloride was added dropwise over 10 min. while maintaining the temperature at 5°-10°. The phases were separated, and the organic phase was dried over anhydrous magnesium sulfate ad filtered to give 772.15 g. (13.2% imidate) of material for a yield of 100.9%. The solvent was removed in vacuo and the residue (53.4% imidate) was stored over 4A molecular sieves.

EXAMPLE 7

A 250 ml, three-necked, round-bottom flask was equipped with a thermometer, magnetic stirrer, drying tube and addition funnel. Into the flask was placed 42.0 g (0.99 M) of the 27.2% solution of ethyl isobutyrimidate from Example 5 along with 70 ml of toluene and 7.15 g (0.01 M) of a 7.61% solution of trimethylamine in toluene. The mixture was cooled to 3° with an ice bath, and a solution of 8.41 g (0.10 M) of diketene in 20 ml of toluene was added dropwise over a 12 min period. The mixture was stirred for 7 min. and the ice bath was removed. The reaction temperature rose to 31° in 15 min. and was subsequently externally cooled to 25°. One hr. and 20 min. after the addition of diketene, the reaction mixture was cooled to 3° and NH₃ was bubbled in for 2.5 hrs., during which the reaction mixture was allowed to warm to r.t. The reaction mixture was then refluxed for 1 hr. and 15 min. with the azeotropic removal of water. The solvent was removed in vacuo to give 14.72 g (92.6% pure oxypyrimidine) of solid for a yield of 90.4% based on the imidate and 89.6% based on diketene.

EXAMPLE 8

250 ml, 3-necked flask was equipped with a magnetic stirrer, thermometer, addition funnel and drying tube. Into the flask was placed 19.0 g (0.10 M) of the 53.4% solution of imidate along with 25 ml of toluene from Example 6 and 7.78 g (0.01 M) of a 7.61% solution of trimethylamine in toluene. The mixture was cooled to 5%, and a solution of diketene (8.41 g, 0.10M) in toluene (25 ml) was added dropwise over a 12 min. period. During the diketene addition the ice bath was removed and the temperature of the reaction mixture rose to 31°. The temperature was maintained at 20°-30° for 1 hr. Toluene (70 ml) was added to the reaction and ammonia was bubbled into the mixture with cooling. After a 2 hr. and 20 min. ammonia treatment, the reaction mixture was refluxed for 1 hr. and 10 min. with water removal. The solvent was removed in vacuo to yield 14.77 g (92.6% oxypyrimidine) of solid for a 90.0% yield.

EXAMPLE 9

A 250 ml, 3-necked flask was equipped with a mechanical stirrer, addition funnel, thermometer, gas inlet tube, and a condenser with water trap. A solution of 15.8 g of ethyl isobutyrimidate in tetrachloroethylene (0.15 mole ethyl isobutyrimidate) containing 0.015 mole of trimethylamine catalyst was charged and to this was added dropwise a solution of 12.66 g (0.16 mole) of diketene in 15 ml of tetrachlorethylene over a 19 minute period. The temperature was maintained at 16°-27° during the addition, and at 25° for 2 hours thereafter. Ammonia gas was passed through the reaction for an additional 2 hours (temp. 25°) and the reaction was heated at reflux for 1.1 hours (final temperature 120°) to remove the H₂O and ethanol produced. The reaction mass was concentrated to dryness giving 23.0 g of solid which contained 91.4% 2-isopropyl-4-methyl-6-oxypyrimidine and resulted in a yield of 92.2%.

EXAMPLE 10

A 500 ml, five-necked, round-bottom flask was equipped with a mechanical stirrer, thermometer, addition funnel and calcium chloride drying tube. Into the flask was placed 116.55 g (0.164 moles) of a 14.2% trichloroethylene solution of methyl isobutyrimidate and 4.86 g (0.0164 moles) of a 19.9% trichloroethylene solution of trimethylamine. The mixture was cooled to 15° and a solution of diketene (13.8 g, 0.1164 moles) in trichloroethylene was rapidly added to the reaction mixture over a 2 minute period. The temperature slowly rose to 30° and the mixture was stirred for 2.5 hours at room temperature. A gas dispersion tube was installed and ammonia was bubbled into the reaction mixture for 2 hours while maintaining the temperature below 25°. A Dean-Stark trap and condenser was installed and the mixture was refluxed with the azeotropic removal of water over a 2 hour period. The solvent was removed in vacuo to yield 24.58 g of solid which contained 86.2% 2-methyl-6-isopropyl-4-oxypyrimidine for a yield of 85.1%

EXAMPLE 11

A 500 ml, 5-necked flask was equipped with a mechanical stirrer, addition funnel, gas inlet tube, thermometer, and a condenser with a water trap. A solution of 50.7 g of (0.1 mole) of ethyl isobutyrimidate in toluene containing 1.01 g (0.01 mole) of triethylamine catalyst was charged, and to this was added dropwise a solution of 8.4 g (0.1 mole) of diketene in 25 ml toluene over a 3 minute period. The temperature was maintained at 20°–29° during the addition, and at 26° for 4 hours thereafter. Ammonia gas was then passed through the reaction for an additional 2.5 hours (temperature 26°) and the reaction was heated at reflux for 1.0 hour (final temperature 110°) to remove the $H_2O$ and ethanol produced. The reaction mass was concentrated to dryness giving 10.98 g of solid which contained 61.6% 2-isopropyl-4-methyl-6-oxypyrimidine and resulted in a yield of 44.5%.

EXAMPLE 12

In a 2-l, 3-necked flask, which was equipped with a mechanical stirrer, thermometer, addition funnel and ice-salt bath were placed 204.34 g of ethyl isobutyrimidate hydrochloride (containing 1 mole of ethyl isobutyrimidate and 2.4 moles of hydrogen chloride) and 300 ml of toluene. To this solution was added 573 g (4.8 moles) of a 49.52% aqueous trimethylamine solution over a 25 minute period while keeping the temperature below 11°. After the layers were separated the aqueous phase was extracted with 100 ml of toluene and the extract was combined with the toluene phase. The excess of trimethylamine and water contained in this phase was removed by azeotropic distillation using a 1 ft. packed column. The dry toluene solution weighed 433.44 g and contained 25.7% of ethyl isobutyrimidate and 0.25 mole % of water. The yield of ethyl isobutyrimidate was 96.6%. To a 250 ml, 3-necked flask, which was equipped with a magnetic stirrer, thermometer, Dean-Stark distilling trap, condenser and drying tube were charged 44.86 g (0.1 mole) of the ethyl isobutyrimidate which had been prepared above and 8.41 g (0.1 mole) of diketene. After the mixture was cooled to 3°, 0.74 g (0.0025 mole) of 20.07% trimethylamine solution in toluene was added. A mild exothermic reaction took place and the temperature rose to 9° in 15 minutes. The ice bath was removed and the reaction mixture was allowed to warm to room temperature. The reaction mixture was stirred for 2 hours and 25 ml of toluene was added and ammonia gas was bubbled in for 2.5 hours while keeping the temperature range 10°–24°. Ammonia sparging was stopped and the reaction mixture was heated to reflux with azeotropic removal of water. Evaporation of the solvent produced 14.9 g of slightly yellow crystalline oxypyrimidine with a m.p. of 161°–170°. The yield was 92.3% (94.3% pure by G.C.).

EXAMPLE 13

The laboratory continuous neutralization unit consists of a stirred, one-liter, jacketed, resin kettle as the neutralization vessel. Ethyl isobutyrimidate hydrochloride, toluene and water are fed to the vessel via FMI metering pumps; trimethylamine (TMA) is sparged as a gas via a rotameter. Overflow from the vessel is pumped to a decanter where the phases are separated. The organic layer is sent from the decanter to a 24"×¾" column packed with ¼" procelain saddles and filled with water for TMA-HCL extraction. The neutralization vessel is initially charged with 240 ml of $H_2O$ and 132 ml of toluene and is cooled to >10°. To the vessel is fed, each hour, 208 g of ethyl isobutyrimidate HCl (Assay-55.3% imidate, 42.4% HCl) as a solution in 202 g of toluene, 214 g of TMA (50% excess based on HCl), 150 g of $H_2O$, and 230 g of toluene. The toluene and ethyl isobutyrimidate HCl/toluene solution lines should join into a common feed line via a mixing tee. Temperature is maintained at 10°–20° C. Volume in the vessel is arbitrarily maintained at ~750 ml. The overflow is fed to the decanter (the overflow line should extend about midway into the resin kettle to insure getting an equal organic-aqueous mix). The aqueous layer is sent to trimethylamine recycle; the organic is sent to the wash column. Water water (~100 g) is changed every two hours. The wash column can be operated in a continuous manner, with the wash water being recycled to the neutralization vessel. The organic layer is dried in the same manner as described for batch neutralization. The yield of ethyl isobutyrimidate is 95°–98°%.

EXAMPLE 14

A 250 ml, three-necked, round-bottom flask was equipped with a magnetic stirrer, thermometer and drying tube. Into the flask was placed diketene (8.82 g, 0.105 M) and 50.22 g (0.1 M) of a 19.75% solution of ethyl isobutyrimidate in toluene. The mixture was stirred and 0.6 g (0.01 M) of glacial acetic acid was added. After fifteen minutes the temperature of the reaction had reached 49° and external cooling was applied. The mixture was stirred for an additional two hours and ammonia gas was introduced. After two hours of ammonia introduction, the reaction mixture was heated for two hours and the solvent was removed under reduced pressure to give 15.81 g (67.0% oxypyrimidine) of solid for a 69.7% yield of 2-isopropyl-6-methyl-4-hydroxypyrimidine.

EXAMPLE 15

A 3-l, 5-necked, round-bottom flask was equipped with a mechanical stirrer, thermometer and drying tube. Into the flask was placed 881.64 g (1.5 mole) of dry ethyl isobutyrimidate in toluene and 132.5 g (1.58 moles) of diketene. The mixture was cooled to 5° and 21.42 g (0.08 moles) of a solution of TMA in toluene was added. The temperature of the reaction mixture was controlled below 30° for a period of 2 hours. A mineral oil bubbler and gas dispersion tube were installed, and the drying tube was removed. Ammonia gas was bubbled into the reaction mixture for a 2 hour period while the reaction temperature was controlled below 30°. At this point, a Dean-Stark trap and condenser were installed, and the introduction of ammonia was discontinued. The reaction mixture was heated at reflux with azeotropic removal of water and ethanol until the vapor temperature reached 108°. The reaction mixture was cooled to room temperature, concentrated HCl (156 g) and $H_2O$ (200 ml) were added and the resulting mixture was vigorously stirred. The phases were separated, and the aqueous phase was placed in a 3-l, 3-necked, bottom outlet reactor which was equipped with a thermometer, mechanical stirrer and external heating. The aqueous phase was then refluxed for 3 hours with azeotropic removal of volatile organics. The mixture was cooled to room temperature and to this solution was added 1,2-dichloroethane (EDC) (1.600 ml) and 50% aqueous NaOH (126 g), respectively. The mixture was heated to 60°, and the phases were separated. The aqueous phase was re-extracted with 200 ml of EDC at 60°, and the organic extracts were combined. The solvent was removed, in vacuo, from the organic phase to yield 209.8 g of a tan solid.

This solid analyzed for 99.2% oxypyrimdine for a yield of 90.8% based on ethyl isobutyrimidate. Another 0.72% of the yield was found in the aqueous phase.

What is claimed is:

1. A method for the preparation of 2-alkyl-4-methyl-6-hydroxypyrimidine of the formula

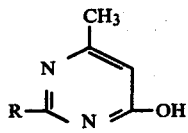

where R represents an alkyl of 1–4 carbon atoms or a cycloalkyl of 3 to 6 carbon atoms which comprises the steps of:
(a) neutralizing an imidate hydrochloride of the formula

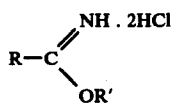

where R' is an alkyl of 1–4 carbon atoms, with a strong acid-accepting base in aqueous solution in the presence of a water-immiscible solvent to form the free imidate;
(b) removing the aqueous phase and any residual water from the solvent/imidate solution phase;
(c) adding a molar equivalent of a solution of diketene in the presence of a Lewis-base or Lewis-acid as catalyst to form an oxazinone of the formula

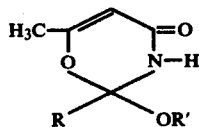

(d) adding gaseous ammonia to said oxazinone solution to form said hydroxypyrimidine;
(e) removing any water formed in step (d); and
(f) removing said solvent and recovering the 2-alkyl-4-methyl-6-hydroxypyrimidine.

2. The method according to claim 1 wherein R is propyl and R' is selected from the group consisting of methyl, ethyl and propyl.

3. The method according to claim 1 wherein said strong base is an inorganic base selected from the group consisting of alkali metal hydroxides and carbonates.

4. The method according to claim 1 wherein said strong base is an acid-accepting organic base.

5. The method according to claim 4 wherein said organic base is selected from the group consisting of trialkylamines of $C_{1-4}$ alkyl and pyridine.

6. The method according to claim 5 wherein said base is trimethylamine.

7. The method according to claim 1 wherein said water-immiscible solvent is selected from the group of liquid, water-immiscible, aromatic and aliphatic hydrocarbons and chlorinated hydrocarbons.

8. The method according to claim 7 wherein said solvent is selected from the group consisting of benzene, toluene, xylene, heptane, 1,1,1-trichloroethane, 1,1,2-trichloroethane, tetrachloroethylene.

9. The method according to claim 8 wherein said solvent is toluene.

10. The method according to claim 1 wherein said residual water is removed by azeotropic distillation.

11. The method according to claim 1 wherein said water removal is by contact of said solvent phase with a solid drying agent selected from the group consisting of molecular sieves and anhydrous drying salts.

12. The method according to claim 1 wherein said miscible solvent for the diketene is selected from the group consisting of toluene, tetrachloroethylene, and trichloroethylene.

13. The method according to claim 1 wherein said Lewis base catalyst is selected from the group consisting of trialkylamines.

14. The method according to claim 13 wherein said trialkylamine is trimethylamine.

15. The method according to claim 1 wherein said free-imidate, diketene and Lewis-base or Lewis-acid catalyst are dissolved in toluene.

16. The method according to claim 1 wherein said water is removed from said 2-alkyl-4-methyl-6-hydroxypyrimidine by azeotropic distillation.

17. The method according to claim 1 wherein ethyl isobutyrimidate hydrochloride is neutralized by trimethylamine dissolved in toluene, the free ethyl isobutyrimidate is freed from water by azeotropic distillation; then the dry ethyl isobutyrimidate in toluene is reacted with an excess of diketene dissolved in toluene in the presence of trimethylamine and the resulting organic solution is treated with gaseous ammonia, in molar equivalent amounts and subsequent azeotropic removal of water to form 2-isopropyl-4-methyl-6-hydroxypyrimidine which is dried and recovered from said organic solvent.

18. The method according to claim 1 wherein 2-alkyl-4-methyl-6-hydroxypyrimidine is extracted with aqueous acid, heated with azeotropic distillation, neutralized and either isolated by filtration or extracted into an organic solvent.

* * * * *